United States Patent … Gotman et al.

(10) Patent No.: US 10,095,904 B2
(45) Date of Patent: Oct. 9, 2018

(54) IMAGE VISUALIZATION

(71) Applicant: KONINKLIJKE PHILIPS N.V., Eindhoven (NL)

(72) Inventors: Shlomo Gotman, Eindhoven (NL); Guy Gilboa, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/888,952

(22) PCT Filed: May 4, 2014

(86) PCT No.: PCT/IB2014/061180
§ 371 (c)(1),
(2) Date: Nov. 4, 2015

(87) PCT Pub. No.: WO2014/181230
PCT Pub. Date: Nov. 13, 2014

(65) Prior Publication Data
US 2016/0117539 A1   Apr. 28, 2016

Related U.S. Application Data

(60) Provisional application No. 61/819,864, filed on May 6, 2013.

(51) Int. Cl.
G06K 7/10 (2006.01)
G06K 7/14 (2006.01)
G06F 19/00 (2018.01)
G16H 40/63 (2018.01)

(52) U.S. Cl.
CPC .......... *G06K 7/1447* (2013.01); *G06F 19/00* (2013.01); *G06F 19/321* (2013.01); *G06K 7/1099* (2013.01); *G16H 40/63* (2018.01)

(58) Field of Classification Search
CPC ............ G06F 17/30879; G06F 21/36; G06F 17/30861; G06F 19/323; H04N 1/00307; H04N 1/00334; H04N 1/00347; H04N 2101/00; H04N 2201/0055; H04N 2201/0084; H04N 2201/3269; H04N 2201/3273; G06K 19/06112
USPC ..... 235/462.01–462.45, 472.01–472.03, 494
See application file for complete search history.

(56) References Cited

U.S. PATENT DOCUMENTS 6,157,373 A  * 12/2000 Rego .................... G02B 27/026
                                                          345/173
7,848,578 B2   12/2010 Suomela et al.
8,073,222 B2   12/2011 Marshall et al.
8,219,570 B2    7/2012 Crucs
(Continued)

FOREIGN PATENT DOCUMENTS

JP   5021912        3/1993
JP   2006304841    11/2006
WO  2013/020198    2/2013

*Primary Examiner* — Thien M Le

(57) ABSTRACT

A method includes at least a portion of an image displayed on a video screen or film, and generating a signal indicative thereof, wherein the at least a portion of the image includes encoded information identifying at least one of a visualization tool or information that are not available without the encoded information, identifying and reading the encoded information, and at least one of invoking the visualization tool or displaying the information identified and read from the encoded information.

15 Claims, 5 Drawing Sheets

(56) References Cited

U.S. PATENT DOCUMENTS

| | | | |
|---|---|---|---|
| 9,203,824 B1* | 12/2015 | Nunn | H04L 63/08 |
| 9,361,657 B2* | 6/2016 | Hunt | G06Q 50/24 |
| 9,655,682 B2 | 5/2017 | Duhamel et al. | |
| 2001/0032101 A1 | 10/2001 | Muller | |
| 2005/0104896 A1* | 5/2005 | Kerr | G06F 19/321 |
| | | | 345/619 |
| 2006/0124742 A1* | 6/2006 | Rines | G06F 17/30879 |
| | | | 235/462.01 |
| 2006/0259463 A1* | 11/2006 | Crucs | G06F 19/321 |
| 2006/0261296 A1* | 11/2006 | Heath | A61B 6/4494 |
| | | | 250/580 |
| 2007/0076938 A1 | 4/2007 | Hartman et al. | |
| 2008/0204236 A1 | 8/2008 | Kraft-Oz | |
| 2009/0212113 A1* | 8/2009 | Chiu | G06K 7/14 |
| | | | 235/462.41 |
| 2009/0217194 A1* | 8/2009 | Martin | G06F 19/3406 |
| | | | 715/783 |
| 2010/0259549 A1* | 10/2010 | Brown | G06F 21/36 |
| | | | 345/589 |
| 2011/0055045 A1* | 3/2011 | Smith | G06Q 30/0621 |
| | | | 705/26.5 |
| 2012/0121124 A1 | 5/2012 | Bammer et al. | |
| 2012/0179908 A1* | 7/2012 | Duma | G06F 19/323 |
| | | | 713/165 |
| 2012/0287460 A1* | 11/2012 | McMillin | H04N 1/00204 |
| | | | 358/1.15 |
| 2012/0304224 A1 | 11/2012 | Hines | |
| 2013/0239104 A1* | 9/2013 | Savant | G06F 21/121 |
| | | | 717/178 |
| 2015/0199751 A1* | 7/2015 | Bryant | G06Q 30/0643 |
| | | | 705/27.2 |
| 2016/0026839 A1* | 1/2016 | Qu | G06F 9/45537 |
| | | | 235/462.15 |

* cited by examiner

IMAGE VISUALIZATION

CROSS-REFERENCE TO PRIOR APPLICATIONS

This application is the U.S. National Phase application under 35 U.S.C. § 371 of International Application No. PCT/IB2014/061180, filed on May 4, 2014, which claims the benefit of U.S. Patent Application No. 61/819,864, filed on May 6, 2013. These applications are hereby incorporated by reference herein.

The following generally relates to viewing images such as computed tomography (CT) images, X-ray images, magnetic resonance (MR) images, positron emission tomography (PET) images, single photon emission computer tomography (SPECT) images, and/or other images.

Images generated in electronic format by systems such as CT, X-ray, MR, PET, SPECT, and/or other imaging systems have been viewed through visualization software executing on a computing system such as a computer. For example, such images have been viewed via a Picture Archiving and Communication System (PACS) and/or the like.

Such systems have been provided by different vendors with basic common viewing capabilities, allowing for similar viewing across systems. Where a particular vendor includes advanced visualization tools with their software and/or customized information in the images, such tools and/or information may not be available and/or accessible via application software of another vendor.

An approach to mitigating such unavailability and/or inaccessibility of the advanced visualization tools and/or customized information is for the vendor to provide an add-on application or the like to the other vendors to run on the other vendors' systems and/or utilize the customized information. This requires concurrently running two different applications from two different vendors in the same software environment without sharing any information.

Unfortunately, the user has to select and load the imaging data twice, one for each application/system, and possibly go back and forth between applications to view and/or manipulate the imaging data, rendering image viewing and/or manipulation tedious and consuming clinician time.

Aspects described herein address the above-referenced problems and others.

The following describes an approach in which information encoded in an image at the time of image generation or thereafter is read and utilized to invoke a visualization tool that is not available without the encoded information and/or to obtain additional information that is not available without the encoded information, allowing the visualization tool and/or the additional information to be accessed essentially by any computing system displaying the image.

In one aspect, a method includes at least a portion of an image displayed on a video screen or film, and generating a signal indicative thereof, wherein the at least a portion of the image includes encoded information identifying at least one of a visualization tool or information that are not available without the encoded information identifying at least one of a visualization tool or information that are not available without the encoded information, identifying and reading the encoded information, and at least one of invoking the visualization tool or displaying the information identified and read from the encoded information.

In another aspect, an image includes a first region in which scanned anatomy is displayed, a second region in which scan information is displayed, and a third region in which no information is displayed, wherein the third region includes encoded information identifying at least one of a visualization tool or additional information that are not available without the encoded information.

In another aspect, a visualization computing system includes a sensor that takes a picture of an image displayed on a monitor or film and generates a signal indicative thereof, wherein the image includes encoded information identifying at least one of a visualization tool or information that are not available without the encoded information, and a processor that scans the signal and extracts the encoded information and at least one of invokes the visualization tool or displays information from the extracted encoded information.

The invention may take form in various components and arrangements of components, and in various steps and arrangements of steps. The drawings are only for purposes of illustrating the preferred embodiments and are not to be construed as limiting the invention.

FIG. 1 schematically illustrates an example visualization computing system.

Figure 1:
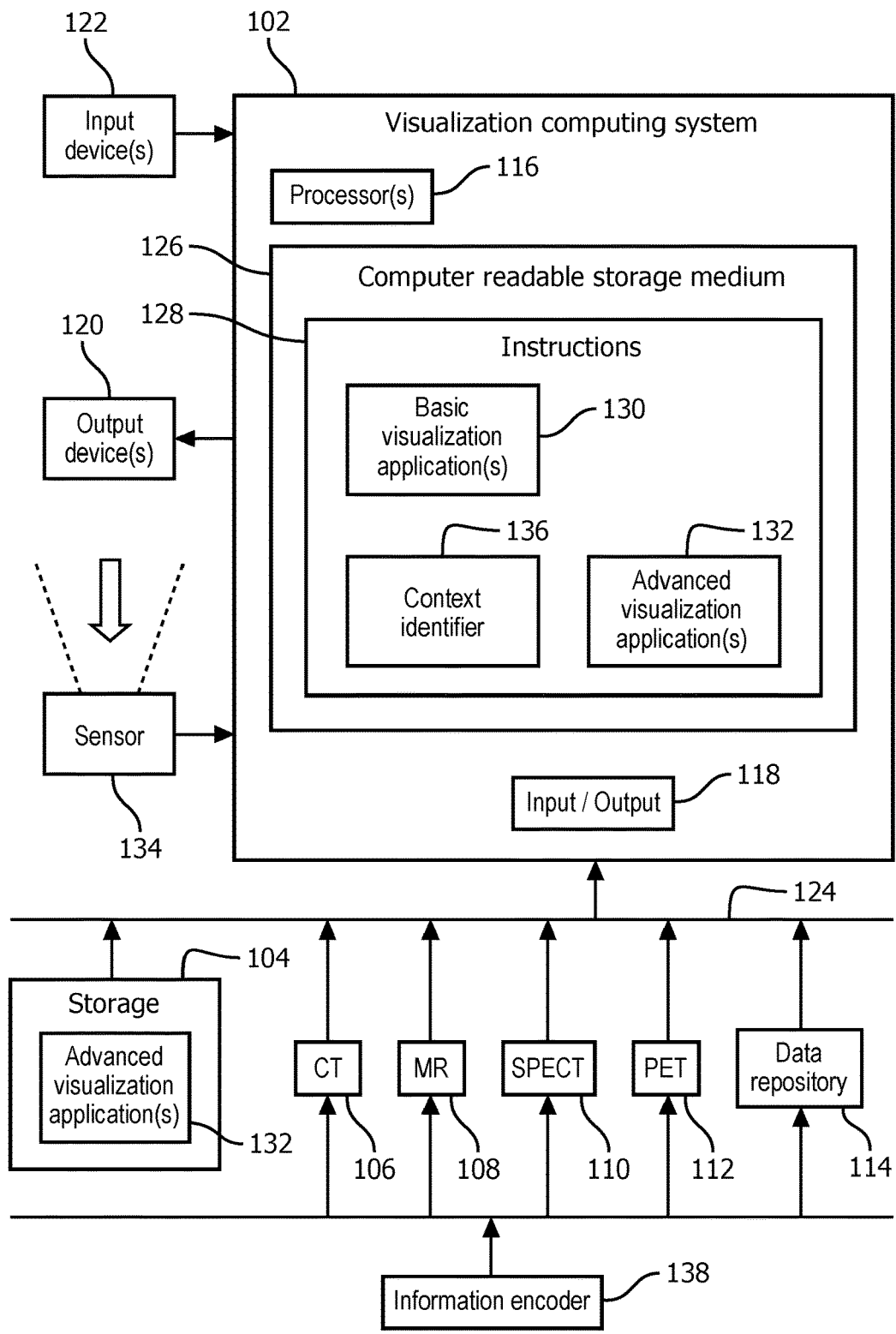

FIG. 1 schematically illustrates a visualization computing system 102 in connection with storage 104 imaging systems, including a CT scanner 106, a MRI scanner 108, a SPECT scanner 110 and a PET scanner 112, and a data repository 114. The visualization computing system 102 can be PACS and/or other computing system.

The visualization computing system 102 includes a microprocessor(s) 116 such as a microprocessor, a central processing unit, a controller, or the like. The visualization computing system 102 further includes input/output (I/O) 118 that facilitates communication with an output device(s) 120 such as a display monitor, filmer, etc., with an input device (s) 122 such as a mouse, keyboard, etc., with a network 124, etc.

The visualization computing system 102 further includes a computer readable storage medium 126, which includes physical memory or other non-transitory memory. The microprocessor(s) 116 executes computer readable instructions 128 encoded or embedded in the computer readable storage medium 126. The microprocessor(s) 116 can also execute computer readable instructions carried by a signal, carrier wave, and other transitory (non-computer readable storage) medium.

The instructions 128 include a basic visualization application(s) 130, which, for this example, include instructions for basic viewing capabilities likely to be common across most vendor computing systems. The instructions 128 further include an advanced visualization application(s) 132, which, for this example, include additional instructions for image viewing and/or manipulating capabilities that are not common to other vendor computing system and/or part of the basic visualization application(s) 130.

The storage 104 likewise includes the advanced visualization application(s) 132. In a variation, only one of the storage or the visualization computing system 102 includes the advanced visualization application(s) 132. The advanced visualization application(s) 132 can be provided to the visualization computing system 102 by the storage 104 and/or otherwise.

For example, the advanced visualization application(s) 132 can be conveyed to the visualization computing system 102 by the storage 104 over the network 124 via a server. In another instance, the advanced visualization application(s) 132 can be obtained from portable memory (e.g., CD/DVD, etc.), etc.

Figure 2:
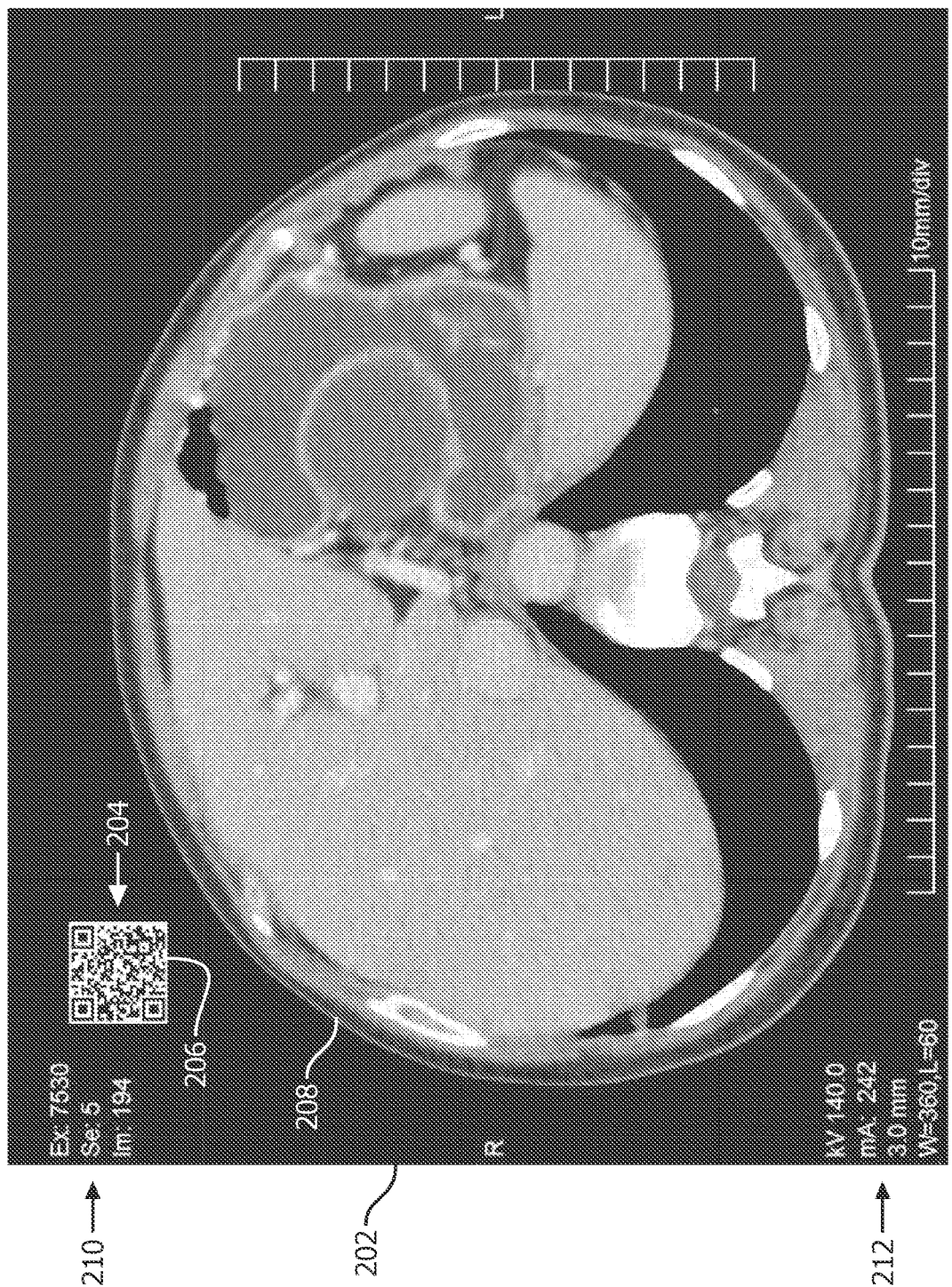
FIG. 2 illustrates an image with encoded information located in a rectangular region.
Figure 3:
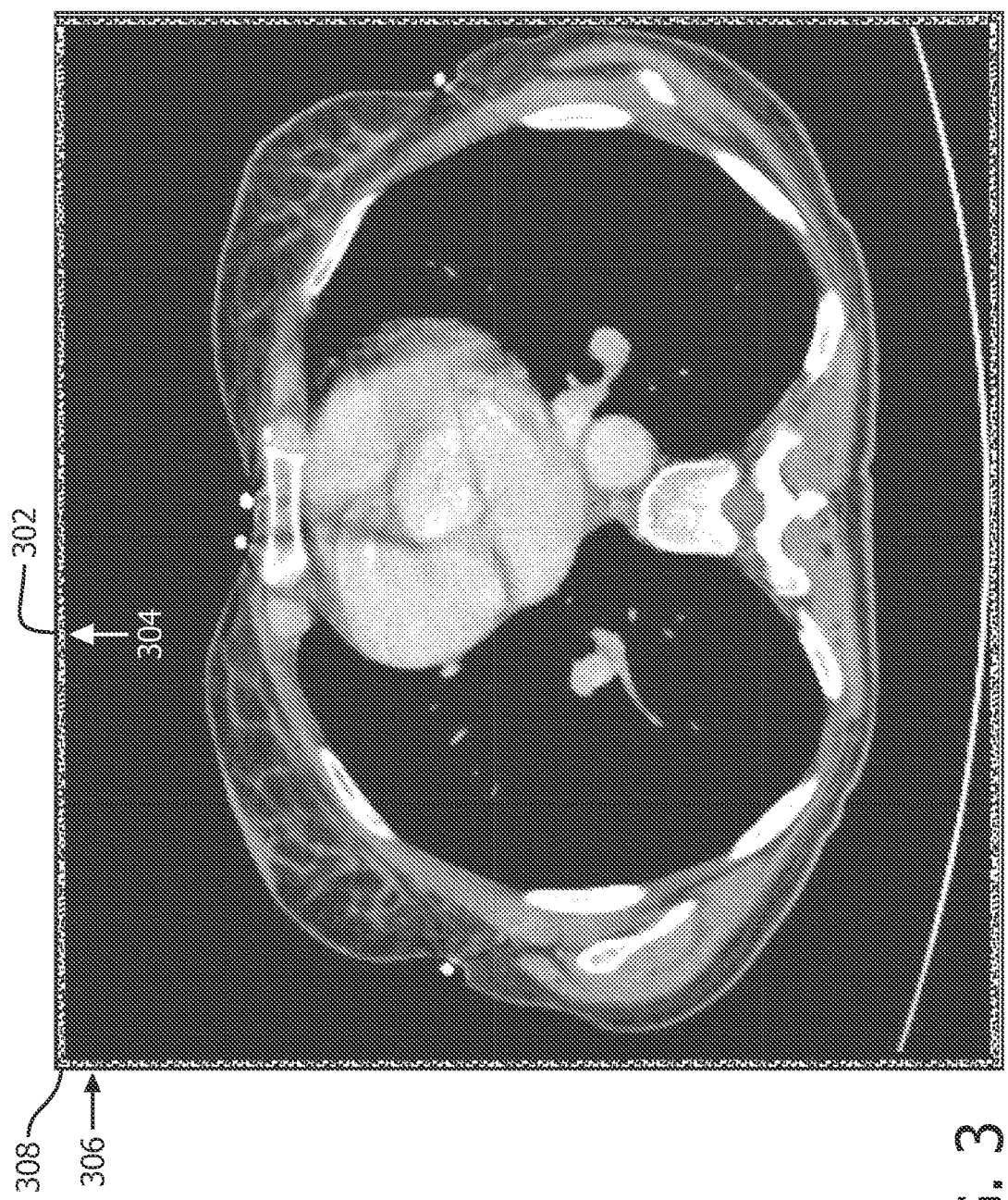
FIG. 3 illustrates an image with encoded information located along a perimeter of the image.

A sensor 134, such as a video or still camera, captures the image displayed via the output device(s) 120 or on film, including information encoded in the image, and generates a signal indicative of the captured encoded information. FIGS. 2 and 3 illustrate examples of images 202 and 302 respectively including encoded information 204 and 304. The encoded information may include information related to invoking the advanced visualization application(s) 132 and/or include other information.

Examples of the other information includes, but is not limited to patient, examination, image number, imaging protocol, acquisition, detection and/or reconstruction including one or more parameters, information in private DICOM fields, post-processing information such as organ and/or bone labeling, computer automated diagnostic (CAD) information related to suspected lesions, bone fractures, etc., fusion of medical data from other imaging modalities, dose contours for radiation therapy planning, source information (e.g., equipment and/or personnel—i.e. a digital signature); dose information (e.g. for dose management software); workflow instructions (i.e. where the image needs to go after further processing, etc.), and/or other information.

In FIG. 2, the encoded information 204 is in a rectangular region 206. As shown in the illustrated example, the rectangular region 206 is located such that it does not cover up any of information 208, 210 or 212 of the image. In FIG. 3, the encoded information 304 is located within a border 306 along a perimeter 308 of the image 302. This may include placing the barcode in N pixels on the edges of the image. Other areas in the images 202 and 302 can include the encoded information 204 and 304.

The encoded information 204 can be "burned" into the images (i.e., replacing the original pixel data), encoded as a separate layer, using standard industry-wide techniques, such as DICOM overlays layer, or DICOM Presentation State object, and/or otherwise encoded. Using such separate layer, the encoded information 204 can be turned on/off as needed.

Returning to FIG. 1, the information is encoded in the image by an information encoder 138. In one instance, encoded information is in a barcode. The barcode can be encoded when and where the image is generated, for instance, by one of the imaging systems 102. Alternatively, the barcode can be added based on information extracted from the image header (e.g., a DICOM header). The encoded information can be proprietary, open, or based on a standard. The amount of information in the code, in one instance, can range from 1 to 2000 bytes of information, e.g., 119 bytes, 1273 bytes, etc.

Figure 5:
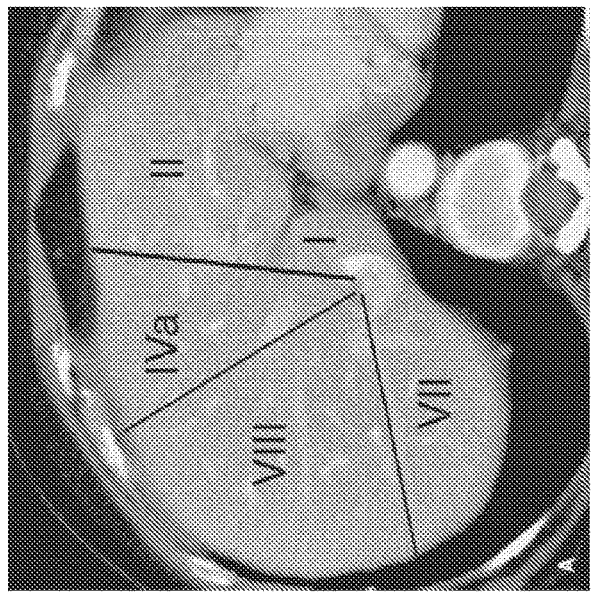
FIG. 5 illustrates an image in which liver segment labeling overlay is extracted from the encoded information and superimposed over the image.
Figure 6:
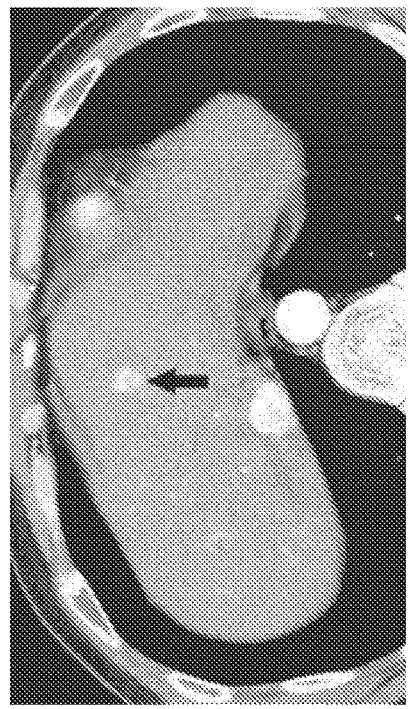
FIG. 6 illustrates an image in which a suspected lesion labeling overlay is extracted from the encoded information and superimposed over the image.
Figure 4:
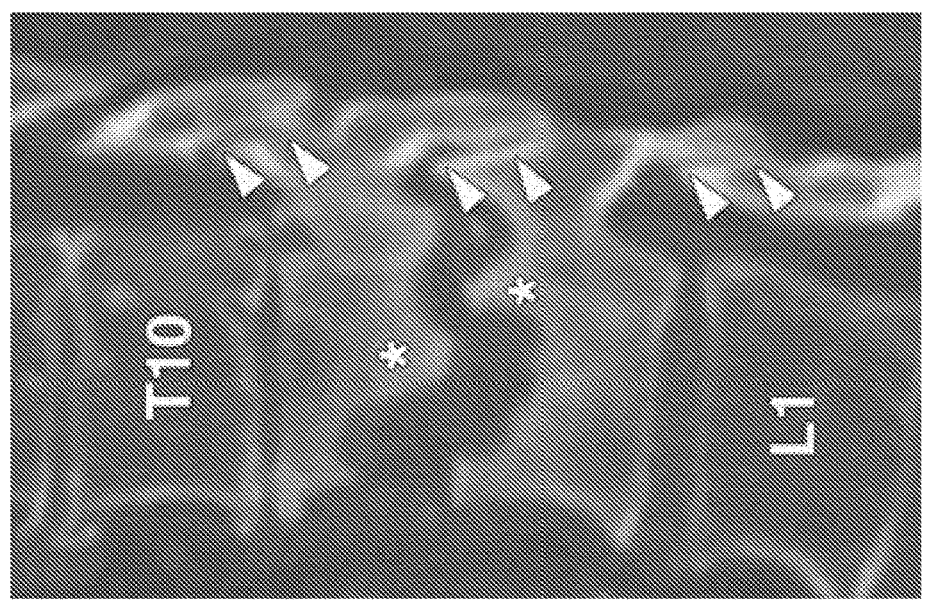
FIG. 4 illustrates an image in which a spine labeling overlay is extracted from the encoded information and superimposed over the image.

The instructions 128 further include a context identifier 136. The context identifier 136 processes the signal and invokes an advanced visualization application of the advanced visualization application(s) 132 related thereto and/or visually presents information extracted from the information encoded in the image. FIGS. 4, 5 and 6 show examples in which overlay information is extracted from the encoded information and visually presented over visually displayed images.

FIG. 4 shows bone labeling of the spine extracted from the encoded information, FIG. 5 shows liver segments extracted from the encoded information, and FIG. 6 shows a suspected liver lesion extracted from the encoded information. For visualization, the context identifier 136 takes into account the location and scale of the images. Since the location of the code and its scale on the screen is known, the context identifier 136 can calibrate automatically these parameters for the overlay.

The encoded information can also be added to medical reports (either electronic or paper) provided to a patient or to his/her referring physician. Later, if needed, this encoded information can be scanned from the report (e.g., using a smartphone reading application, etc.) and the related image is retrieved from a remote storage and displayed.

Returning to FIG. 1, in one non-limiting instance, the context identifier 136 first identifies a place where there is no useful clinical data and outside the anatomy. The context identifier 136 scans the image to find the barcode inset using well-known anchor areas of the encoded information. An example approach includes the commonly known technique used in connection with smartphones, tablet computers, or the like. Using coding with a high level of redundancy and error correction mitigates instances where a portion of the barcode is covered by some of the overlay.

The context identifier 136 can be conveyed to the visualization computing system 102 over the network 124 via a server. In another instance, the advanced visualization application(s) 132 can be obtained from portable memory (e.g., CD/DVD, etc.), etc.

The encoded information allows applications and/or information not directly related to or integrated with the displaying system to identify the currently displayed image(s) and to use this context for their own purposes. In one instance, this mitigates having to integrate visualization applications of different vendors and/or comply with a standard by multiple different vendors. For instance, encoded information does not require any configuration and works seamlessly with any system.

The illustrated visualization computing system 102 obtains imaging data from one or more of the imaging systems 106, 108, 110 and 112, other imaging system, the data repository 114, and/or other device and/or storage. The data repository 114 may include one or more of a radiology information system (RIS), a hospital information system (HIS), an electronic medical record (EMR), a sever, a database, and/or the like.

The visualization computing system 102 can be activated to determine the context of the image in response to a user activating the visualization computing system 102 to do so, e.g., when the user determines they want to use the advanced visualization application(s) 132. In another instance, the visualization computing system 102 determines the context when the basic visualization application is employed and stores the context information for later use.

The encoded information can be modified and/or update, for example after further processing. Furthermore, the updated encoded information can be overlaid over encoded information, for example, to maintain a history of the encoded information.

Figure 7:
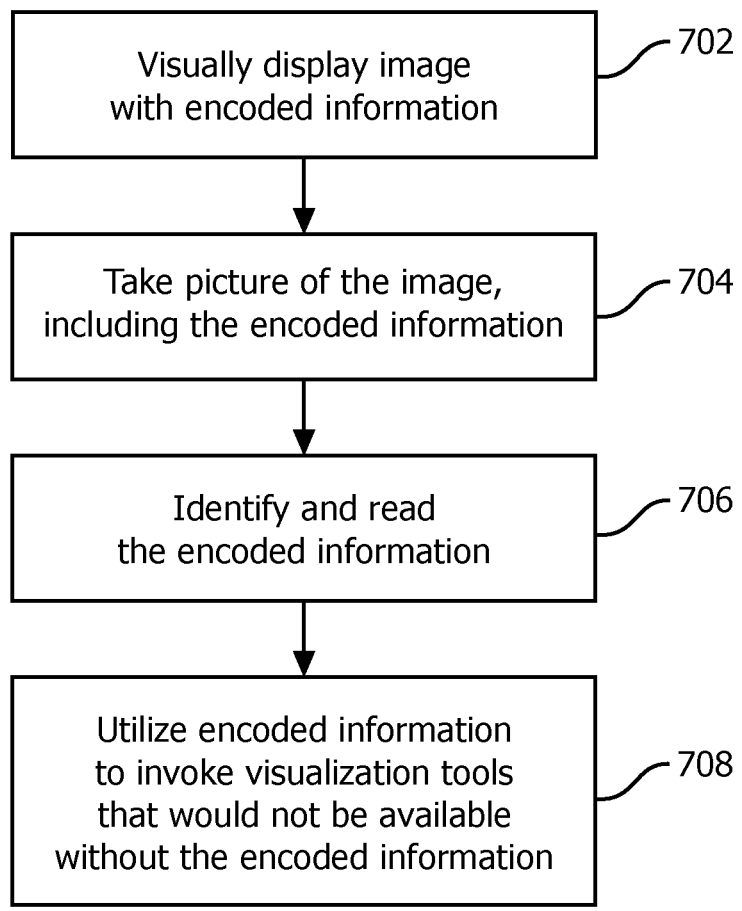
FIG. 7 illustrates an example method in accordance with the embodiments herein.

FIG. 7 illustrate an example method.

It is to be appreciated that the ordering of the acts in the methods is not limiting. As such, other orderings are contemplated herein. In addition, one or more acts may be omitted and/or one or more additional acts may be included.

At 702, an image, including encoded information, is visually displayed via the visualization computing system. Alternatively, the image can be on a film hung on a viewing box.

At 704, a camera or the like takes a picture of at least a portion of the image, including the encoded information, and generates a signal indicative thereof.

At 706, the encoded information is identified and read.

At 708, the encoded information is utilized for invoking visualization tools, which would not otherwise be available without the encoded information.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
    capturing, with a camera, at least a portion of a medical image displayed on a video screen or film, and generating a signal indicative thereof, wherein the at least the portion of the medical image includes encoded information in a barcode identifying a software visualization application not available without the encoded information and the barcode further includes encoded additional information about the medical image, wherein the encoded additional information is located in the barcode along a perimeter, and the barcode is located on at least three sides of the medical image with scanned anatomy bounded by the perimeter;
    identifying and reading the encoded information; and
    executing the computer executable instructions of the software visualization application read from the encoded information.

2. The method of claim 1, wherein the encoded additional information about the medical image comprises at least one from the group comprised of:
    patient information;
    examination information;
    an image number;
    an imaging protocol;
    at least one imaging modality acquisition parameter;
    at least one imaging modality detection parameters;
    at least one imaging reconstruction parameter;
    information from at least one private DICOM field;
    an organ label;
    a bone label;
    computer automated diagnostic information related to suspected lesions;
    computed automated diagnostic information related to bone fractures;
    medical data fused from an imaging modality;
    dose contours for radiation therapy planning:
    a digital signature;
    dose information; and
    workflow instructions.

3. The method of claim 1, wherein the barcode is added to the image at the time the medical image is generated by a medical imaging scanner.

4. The method of claim 1, wherein the barcode is added to the image after the medical image was generated by a medical imaging scanner, wherein the barcode replaces original pixel data of the medical image.

5. The method of claim 1, wherein the barcode includes 100 to 2000 bytes of data.

6. The method of claim 1, wherein the barcode is located in a rectangular region of the medical image where no anatomical or overlay information is located.

7. The method of claim 1, wherein the barcode is located along a rectangular perimeter of the medical image, and the barcode is located on four sides of the medical image.

8. The method of claim 1, wherein the encoded additional information includes encoded overlay information, and further comprising:
    superimposing overlay information decoded from the encoded overlay information over the displayed medical image, wherein the overlay information overlays at least a portion of imaged anatomy in the displayed medical image.

9. The method of any claim 1, wherein the visualization tool is located on a computing system displaying the image.

10. The method of claim 1 wherein the visualization tool is located remote from a computing system displaying the image and accessed over a network.

11. A medical image, comprising:
    a first region in which scanned anatomy is displayed; and
    a second region in which no scanned anatomy is displayed, wherein the second region includes encoded information identifying a software visualization application to run, wherein the software visualization application is not available without the encoded information, wherein the encoded information is located in a barcode along a perimeter, and the barcode is located on at least three sides of the medical image with the scanned anatomy bounded by the perimeter.

12. The image of claim 11, wherein the barcode includes 100 to 2000 bytes of data.

13. The image of claim 11, wherein the encoded information further includes overlay information that is encoded with the encoded information, and the overlay information defines an overlay for scanned anatomy of the medical image.

14. The image of claim 11, wherein the visualization tool is located on a computing system displaying the image.

15. The image of claim 11, wherein the visualization tool is located remote from a computing system displaying the image and accessed over a network.

* * * * *